United States Patent
Konofal

(10) Patent No.: US 10,532,100 B2
(45) Date of Patent: Jan. 14, 2020

(54) USE OF IRON FOR TREATING ATTENTION DEFICIT HYPERACTIVITY DISORDER IN CHILDREN

(75) Inventor: Eric Konofal, Paris (FR)

(73) Assignee: NLS PHARMA AG, Stans (CH)

( * ) Notice: Subject to any disclaimer, the term of this patent is extended or adjusted under 35 U.S.C. 154(b) by 2016 days.

(21) Appl. No.: 10/559,293

(22) PCT Filed: Jun. 1, 2004

(86) PCT No.: PCT/FR2004/001351
§ 371 (c)(1),
(2), (4) Date: Jan. 19, 2006

(87) PCT Pub. No.: WO2004/105744
PCT Pub. Date: Dec. 9, 2004

(65) Prior Publication Data
US 2006/0147552 A1    Jul. 6, 2006

(30) Foreign Application Priority Data
May 30, 2003    (FR) ...................... 03 06581

(51) Int. Cl.
*A61K 45/06*    (2006.01)
(52) U.S. Cl.
CPC ................... *A61K 45/06* (2013.01)
(58) Field of Classification Search
CPC ....... A61K 33/26; A61K 31/295; A61K 45/06
See application file for complete search history.

(56) References Cited

PUBLICATIONS

Bruner et al. (Lancet. 1996, 348, 992-996), Randomised study of cognitive effects of iron . . . .*
Arnold (Annals New York Academy of Sciences, 2001, 931, 310-341), Alternative treatments for adults with . . . .*
Overtoom et al. (Behavioral Brain Research 2003, 154, 7-15), Effects of methylphenidate.*
Konofal et al. Pediatric Neurology 2008, 38, 20-2; Effects of iron supplementation on attention . . . .*
Rowland et al. MRDD Research Reviews 2002, 8, 162-170; The epidimology of attention . . . .*
Beguin Clinica. Chimica. Acta., 329, 9-22, 2003; Soluble transferrin receptor for . . . .*
The definition of "Child" the online Cambridge Advanced Learner's Dictionary (last accessed Jul. 2010).*
Yehuda et al. (Am. J. Clin. Nutr. 50, 618-629, 1989) Brain iron: a lesson from animal models.*
Goldman et al. (Journal of American Medical Association, 279 (14), 1100-1107, 1998) Diagnosis and Treatment of Attention-Deficit . . . .*
Horvath et al. (Ther Hung 1992, 40 (1), abstract) Tardyferon therapy in . . . .*
Solanto (Behavior rain Research 1998, 94, 127-152) Neuropsychopharmacological mechanisms of stimulant . . . .*
Sever et al. (1997) *Neuropsychobiology* vol. 35, No. 4, pp. 178-180.
Davis et al. (2000) *European Neurology* vol. 43, No. 2, pp. 70-75.
Burattini et al. (1990) *Minerva Pediatrica* vol. 42, No. 9, pp. 343-347.
O'Keeffe et al. (1994) *Age and Ageing* vol. 23, No. 3, pp. 200-203.
Sun et al. (1998) *Sleep* vol. 21, No. 4, pp. 371-377.
Schauss (1984) *Nutrition and Health* vol. 3, No. 1-2, pp. 9-37.
Ward (1997) *Journal of Nutritional and Environmental Medicine* vol. 7, No. 4, pp. 333-342.
Walther (2002) *Expert Opinion on Investigational Drugs*, vol. 11, No. 4, pp. 501-514.
Diagnostic and Statistical Manual of Mental Disorders, 4th Edition, American Psychiatric Association, 1994, pp. 83-85.

* cited by examiner

*Primary Examiner* — Tigabu Kassa
(74) *Attorney, Agent, or Firm* — Norton Rose Fulbright US LLP

(57) ABSTRACT

The invention relates to the use of iron for preparing a medicament for the preventive and/or curative treatment of attention deficit hyperactivity disorder (ADHD) or at least one of the symptoms thereof, for a patient requiring such treatment.

9 Claims, 1 Drawing Sheet

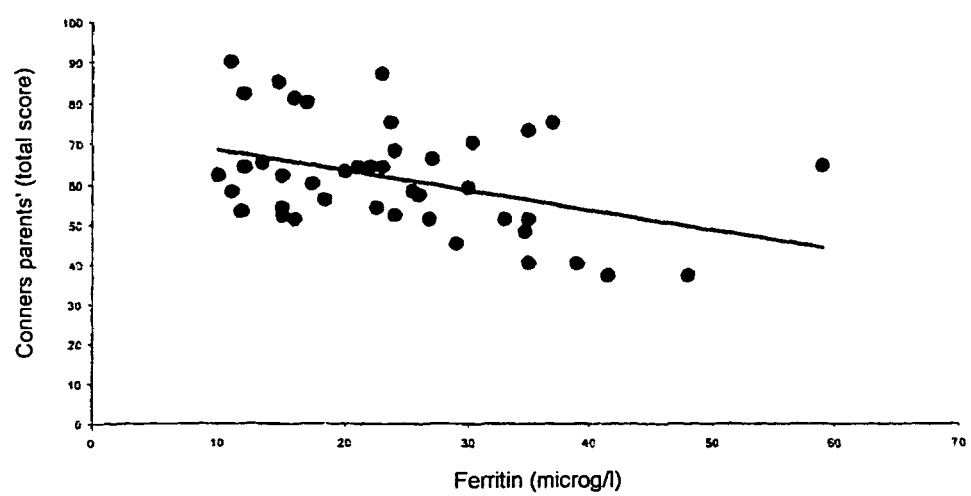

USE OF IRON FOR TREATING ATTENTION DEFICIT HYPERACTIVITY DISORDER IN CHILDREN

The present invention relates to the field of human health, and more particularly to the treatment of "attention deficit hyperactivity" disorder. More particularly, the present invention relates to the use of iron or of a pharmaceutically acceptable salt thereof, alone or in combination with one or more psychostimulant compounds, for preparing a medicinal product for use in the treatment of ADHD and of the associated symptoms.

"Attention deficit hyperactivity" disorder in children (ADHD) is a behavioral disorder that constitutes the primary reason for a consultation in psychology for children and adolescents. This very widespread syndrome affects 6 to 10% of children of school age.

In clinical terms, this disorder combines inattention, impulsiveness and motor-hyperactivity unsuitable for the child's environment. Badly organized and absent minded, these children sometimes in the end no longer follow in class. The excessive motor agitation, which is incompatible with social relationships and which can sometimes even result in the child dropping out of the school system prematurely, is probably the symptom that will lead the parents to consult a specialist.

The physiopathology of this disorder still remains today disputed, although, for a large number of authors, the hypothesis of dopaminergic and noradrenergic system involvement appears to be validated [Spencer et al., Pharmacotherapy of attention deficit hyperactivity disorder. Child Adolesc Psychiatr Clin N Am. 2000; 9(1): 77-97]. This dysfunction of dopaminergic neurotransmission appears to be involved in the symptoms of excessive motor hyperactivity characteristic of ADHD in children. In fact, the improvement in the motor hyperactivity with dopaminergic psychostimulants is often very significant, but nevertheless insufficient.

Insomnia, difficulties in falling asleep, waking up during the night, possibly due to excessive nocturnal motor agitation, and also attention disorders, such as inattention, impatience and impulsiveness, appear to evade all forms of treatment [Chervin et al., Associations between symptoms of inattention, hyperactivity, restless legs, and periodic leg movements. Sleep 2002 15; 25(2): 213-8; Gruber et al., instability of sleep patterns in children with attention-deficit/hyperactivity disorder. J Am Acad Child Adolesc Psychiatry. 2000; 39(4): 495-501].

There exists therefore a real need to develop novel treatments for ADHD which make it possible to obtain better results than those obtained with the current psychostimulant-based treatments, and in particular make it possible to treat the symptoms that evade the current treatments. This is the aim of the present invention.

Entirely fortuitously, the inventor has now observed an abnormally low blood ferritin level in children suffering from ADHD. The inventor has also demonstrated a correlation between the severity of the symptoms and the blood ferritin level. The present invention therefore proposes to provide a preventive and curative treatment for ADHD by correcting the low blood ferritin level observed in these patients.

In the past, various studies were carried out which led to the involvement of iron in ADHD being studied. The basis of these studies is the observation that children suffering from ADHD have a low concentration of certain trace elements, including iron (for review see: Brue and Oakland, 2002 Alternative Therapies 8: 68-73). Thus, in 1994, Kozielec et al. (Psychiatr. pol. 28: 345-353) looked for a deficiency in trace elements (magnesium, zinc, copper, calcium, iron) in ADHD. The authors did not make the connection between iron and ADHD and, conversely, the blood magnesium level found in the children studied prompted the authors to mention the advantage of giving a magnesium supplement in ADHD. The existence of excessive nocturnal locomotion led Sever et al. (1997, Neuropsychobiology 35: 178-180) to study the involvement of iron in ADHD in children who are not anemic. This study, which remains the only study that focused on showing the advantage of treating children with ADHD empirically, does not evoke, either in its results or in its perspectives, the role of ferritin in the physiopathology of the disorder. The results obtained do not show any relationship between the severity of the symptoms and iron-related deficiency. The authors concluded, moreover, that iron deficiency does not play a role in the physiopathology of ADHD and that oral treatment with iron in children affected by ADHD is not recommended. Finally, these inconsistent and sometimes contradictory results obtained by researchers and physicians have led them to prefer other therapeutic approaches for ADHD, which are currently ongoing, based in particular on dopaminergic psychostimulants.

A subject of the present invention is therefore the use of iron, or of a pharmaceutically acceptable salt thereof, for preparing a medicinal product for use in the preventive and/or curative treatment of attention deficit hyperactivity disorder (ADHD) or of at least one of the symptoms thereof in a patient requiring such a treatment. Ferritin is an iron storage protein (Connor et al., Pediatric Neurology 25: p 123-124).

In the context of the present invention, the diagnosis of attention deficit hyperactivity disorder (ADHD) is based on the clinical characteristics defined by the international classification, Diagnostic and Statistical Manual of mental disorders, DSM-IV ($4^{th}$ edition, 1994).

The DSM-IV criteria include three dimensions (inattention, impulsiveness and hyperactivity), and a normal intellectual efficiency (IQ>80), but include no organic nor neurological pathology.

In the case of the present invention, the patient is therefore a child with an IQ>80, between 5 and 12 years old, and who exhibits an isolated iron-related deficiency but is not anemic, i.e. exhibits a normal hemoglobin level. The expression "iron-related deficiency" is intended to mean a low blood ferritin level without significant modification of the serum concentration of soluble transferrin receptors.

For the purpose of the present invention, the term "iron" is intended to mean iron in the form of an iron atom, an iron salt or organic iron, or any formulation containing iron, that is pharmaceutically acceptable. By way of a nonexhaustive list, the pharmaceutically acceptable iron salt is selected from ferrous salts and ferric salts, preferably from ferric ammonium citrate, ferric pyrophosphate, ferrocholinate, ferrous ascorbate, ferrous aspartate, ferrous chloride, ferrous sulfate, ferrous tartrate, ferrous fumarate, ferrous gluconate, ferrous gluceptate, ferrous glycine sulfate, ferrous lactate, ferrous oxalate and ferrous succinate. According to a preferred embodiment of the invention, the iron salt is ferrous sulfate, and preferably gastroprotected ferrous sulfate such as the speciality product "Tardyferon" from the Laboratoires Pierre Fabre Medicament. Alternatively, the pharmaceutically acceptable iron is in the form of iron dextran, iron sucrose, iron polymaltose or iron sorbitol. When the iron is in the form of pharmaceutically acceptable organic iron, it is preferably iron biglycinate, iron glycinate or iron protein succinylate.

The nature of the salt administered to the patient depends on the route of administration selected, which may, without distinction, be oral, anal, parenteral, intravenous or intramuscular administration. It is preferably oral administration.

The term "ADHD symptoms" is intended to denote in particular the attention disorders such as inattention, impulsiveness, impatience, oppositional disorders, but also diurnal and nocturnal motor hyperactivity, and insomnia. The term "insomnia" is intended to denote:

a. sleep onset insomnia, which is characterized by difficulties in falling asleep;
b. sleep maintenance insomnia, which is characterized by nocturnal motor-hyperactivity and waking up during the night, and
c. psychopathological insomnia, which is generally chronic and generally related to anxiety, to stress and to depressive episodes.

According to a preferred embodiment, the use of iron or of a pharmaceutically acceptable salt thereof according to the invention is carried out in combination with at least one compound selected from psychostimulants, as a combination product for use simultaneously, separately or spread out over time.

The term "psychostimulant compounds" is intended to denote dopamine and/or noradrenaline uptake inhibitors. Among these, mention should be made, in a nonexhaustive capacity of L-Dopa, dopamine, L-dopa agonists, rotaline. More particularly, the psychostimulant compounds are chosen from methylphenidate (speciality product Ritalin), modafinil, atomoxetine, and amphetamines, such as d-amphetamine, dexedrine or dexamphetamine.

The present invention also relates to the use of iron, or of a pharmaceutically acceptable salt thereof, in combination with at least one compound selected from psychostimulants, in particular dopamine and/or noradrenaline uptake inhibitors, as a combination product for use simultaneously, separately or spread out over time, for preparing a medicinal product for use in the preventive and/or curative treatment of a pathology selected from ADHD or at least one of the symptoms of ADHD, such as nocturnal and/or diurnal motor hyperactivity. The pharmaceutical composition comprising this combination and pharmaceutically acceptable excipients is also part of the invention.

In the context of the present invention, the dosage with respect to iron corresponds to a daily intake of ferrous sulfate of between 0.1 mg and 10 g, and preferably of between 10 mg and 2 g per day, and more particularly of at least 50 mg, at least 150 mg, at least 200 mg, at least 250 mg, at least 300 mg, at least 350 mg, at least 400 mg, at least 450 mg, at least 500 mg, at least 550 mg, at least 600 mg, at least 700 mg, at least 800 mg, at least 900 mg, at least 1 g per day, preferably of between 400 mg and 750 mg per day, preferably approximately 500 mg, in one or more daily intakes.

The patient according to the invention is chosen from a newborn, a child, an adolescent and an adult. According to a preferred embodiment, it is a child approximately 5 to 12 years old, and/or an adolescent. The patient according to the invention is affected by an iron-related deficiency but is not anemic, i.e. the patient does not show a decreased hemoglobin level. The expression "iron-related deficiency" is intended to mean a low blood ferritin level without significant modification of the serum concentration of soluble transferrin receptors. The ferritin deficiency can be measured in the serum, but also in any other biological fluids such as cerebrospinal fluid.

A ferritin deficiency corresponds to a serum concentration of ferritin in the adult patient of less than approximately 50 µg/liter. This low blood ferritin level can reach ferritin concentrations of less than approximately 40 µg/l, or even less than approximately 35 µg/l, less than approximately 30 µg/l, less than approximately 20 µg/l, less than approximately 15 µg/l, or even less than approximately 10 µg/l. The techniques for assaying serum ferritin are well known to those skilled in the art. Mention may be made of the immunoenzyme method (IMX ferritin kit, Abott Laboratories).

The patient according to the invention also exhibits a normal serum concentration of soluble transferrin receptors. Transferrin is involved in the acquisition of iron by the body's cells; this acquisition is controlled by the number of transferrin receptors that exist at the cell surface. The concentration of these receptors can be evaluated by techniques known to those skilled in the art, such as nephelemetry (Ruivard et al., 2000 Rev. Med. Interne 21: 837-843). A normal concentration range for soluble transferrin receptors is 2.0-4.50 mg/l for men and 1.80-4.70 mg/l for women (see RsTF kit ref. 2148315 from Roche).

The role of iron in the central nervous system is often reported in fundamental as in clinical neurophysiopathology. Functional or intellectual asthenia, chronic fatigue syndrome, or, conversely, psychomotor instability and irritability may be the result of an iron-related deficiency (Lozoff, 1989 Adv Pediatr 1989; 6: 331-59). The role of iron in the physiopathology of neurological diseases, and in particular in idiopathic Parkinson's disease, has been known for more than thirty years. The evidence of an increase in iron in particular in certain brain structures (for example, dentate nucleus) in rare neurodegenerative pathologies (for example, Friedrich's ataxia) is also known. More recently, the role of transferrin receptors in certain neurophysiopathological processes has just been documented (Marder K, et al. 1998 Neurology 50, 4: 1138-40). An increase in transferrin receptor number in the endothelium cells of brain capillaries could be responsible for the cytoplasmic accumulation of iron in the cells of the neurons of the basal ganglia (globus pallidus, substantia nigra, red nucleus and dentate nucleus). Transferrin receptor dysfunction due to hyperplasia (increase in receptor number) at the central level would explain the accumulation of iron in certain structures involved in neurodegenerative phenomena. Conversely, a decrease in these receptors would contribute to protecting the central nuclei against the phenomenon. In the event of there being a decrease in plasma ferritin in the physiopathology of ADHD, a physiological increase in transferrin receptors should occur, as it occurs normally in the case of anemia, so as not to subject the brain structures to an iron-related deficiency. On the other hand, an absence of response (no increase in the number of transferrin receptors) would lead to a decrease in iron in the brain and would be compatible with a dopaminergic dysfunction due to a decrease in dopamine synthesis and/or in the stimulation of dopaminergic receptors. The present invention therefore also relates to the use of iron, or a pharmaceutically acceptable salt thereof, for the preventive treatment of a newborn, child, adolescent or young adult patient led to develop, at an adult age, a neurodegenerative pathology, characterized in that said newborn, child, adolescent or young adult patient exhibits at least the following symptoms:

a ferritin deficiency, such that the serum of ferritin concentration is less than 50 µg/l, a normal serum concentration of soluble transferrin receptors, an attention deficit hyperactivity disorder, or at least one of the symptoms thereof.

Preferably, said patient is a child with an IQ>80, who is between 5 and 12 years old and is not anemic.

Preferably, said neurodegenerative pathology is Parkinson's disease, cerebellar ataxia, Friedrich's ataxia, Alzheimer's disease, Huntington's chorea, or amyotrophic lateral sclerosis. More particularly, it is Parkinson's disease.

In addition, the present invention also relates to any diagnostic method or kit using ferritin and/or iron and soluble transferrin receptors as a marker for ADHD severity. This is the reason for which the invention also provides an in vitro method for the prognosis and/or diagnosis of attention deficit hyperactivity disorder, comprising the step of quantitatively evaluating, in a patient suspected of being affected by said disorder, the serum ferritin concentration and the soluble transferrin receptor concentration, such that a serum ferritin concentration of less than 50 µg/l and a normal physiological concentration of soluble transferrin receptors indicates that the patient is or will be affected by said disorder. The corresponding diagnostic kit is also a subject of the present invention.

Finally, the invention is aimed at protecting a source of iron alone or in combination with at least one psychostimulant, preferably ritalin, as a medicament or as active principles of a pharmaceutical composition comprising pharmaceutically acceptable excipients, for the preventive and/or curative treatment of ADHD or a symptom thereof.

Other characteristics, aims and advantages of the invention will emerge from the examples that follow. The invention is not limited to the specific examples mentioned simply by way of illustration and which should be read with regard to the following figure:

FIG. 1:

The ferritin values (normal=34 µg/l) are inversely correlated (p<0.01) with the severity of the ADHD symptoms, expressed by the Conners Parents' scale (normal<50).

EXAMPLES

1. Method

Forty-three children, 36 boys and 7 girls, with an average age of 9.2±2.2 participated in this prospective study. Their clinical characteristics corresponded to the ADHD criteria of the diagnostic and statistical manual of mental disorders (4$^{th}$ edition, APA, 1994). These ADHDs were confirmed by means of a structured interview (history). The children were suffering from no physical deficiency, nor from malnutrition, nor from mental (IQ>80) or organic diseases, and were receiving no treatment that included an iron supplement or psychostimulants, for a period of at least 2 months before the study.

The seriousness of the symptoms was evaluated using the Conners evaluation scale (parents' questionnaire), including for the subscales for evaluation of cognitive capacities and of oppositional disorder. The blood ferritin level was measured, as were the hemoglobin level, the hematocrit and the serum iron, by conventional methods (Elecsys tests, immunoenzymology). The mean values for ferritin were classified in three groups: normal (>34µg/l), subnormal (>15 µg/l) and abnormal (<15 µg/l).

2. Results

The mean result of all the patients (61±13) subjected to the Conners parents' questionnaire revealed serious ADHDs. This result was identical in the girls (63±8) and in the boys (60±14). The serum iron (group mean: 84±36 µg/100 ml), and the hemoglobin and hematocrit levels were normal. The mean blood ferritin value was low (25±12 µg/l) and in particular pathological in 33 out of 43 children exhibiting an ADHD (77%). It was identical in the boys (26±13 µg/l) and in the girls (19±8 µg/l), and it was not related to age.

The relationships between the clinical and biological characteristics of the patients, as a function of their blood ferritin level (abnormal, subnormal and normal), are reported in Table 1. The children having an abnormal ferritin exhibited more serious clinical symptoms for ADHD than the children having a normal ferritin (p<0.01).

Furthermore, there was a negative correlation between the Conners parents' questionnaire and the ferritin values (r=−0.41, p=0.01). There was no correlation between the Conners parents' questionnaire scores for the hyperactivity, cognitive disorder and oppositional disorder symptoms, and the ferritin values.

TABLE 1

Clinical and biological characteristics in the, various groups of children exhibiting ADHD.

| | Mean ferritin values | | |
|---|---|---|---|
| | Low (<15 µg/l) | Subnormal (>15 µg/l) | Normal (>34 µg/l) |
| Patient characteristics | | | |
| Number | 11 | 22 | 10 |
| Age | 9.1 ± 2.5 yrs | 9.6 ± 2.1 yrs | 8.7 ± 2.2 yrs |
| Sex (M/F) | 8/3 | 18/4 | 10/0 |
| Conners parental score | | | |
| Total | 66 ± 13* | 63 ± 11* | 52 ± 14* |
| "Hyperactivity" score | 19 ± 4 | 19 ± 4 | 17 ± 4 |
| "Cognitive disorder" score | 10 ± 4 | 9 ± 4 | 8 ± 5 |
| "Oppositional disorder" score | 8 ± 3 | 9 ± 2 | 7 ± 2 |
| Serum iron (µg/100 ml) | 86 ± 27 | 81 ± 40 | 92 ± 44 |
| Ferritin (µg/l) | 13 ± 2 | 23 ± 5 | 43 ± 11 |

The data are indicated as: mean ± standard deviation.
*p < 0.015, difference statistically significant compared with children with a normal blood ferritin level.

The inventor demonstrated that a low blood ferritin level corresponds to low iron stores in the children suffering from ADHD. The breaking point for iron deficiency in children (between 5 and 12 years old) is a serum ferritin level of greater than 15 µg/l, and affects 3% of them. On the other hand, in our study, 23% of the children with ADHD showed severe iron deficiencies without anemia. In addition, it appears that the ferritin values were inversely correlated with the severity of the symptoms, expressed by means of the Conners parents' questionnaire. This implies that a relationship exists between iron stores (ferritin) and ADHD symptoms.

It therefore appears to be important to initiate control of the body's iron stores (blood ferritin level) systematically in specialist consultation for ADHD. The search for an iron-related deficiency in ADHD and its therapeutic control should in fact precede the administration of a psychostimulant.

The invention claimed is:

1. A method for the treatment of attention deficit hyperactivity disorder (ADHD) as defined in the DSM IV in a patient in need thereof comprising administering an effective amount of an iron supplement in the form of a pharmaceutically acceptable iron salt or organic iron or iron atom to said patient wherein said patient is a child of between 5 and 12 years old affected by a ferritin deficiency with a serum ferritin concentration of less than 50 μg/L, and who also has a normal serum concentration of soluble transferrin receptors, and wherein iron is administered in a dosage that corresponds to a daily intake of ferrous sulfate of between 100 mg and 2 g per day, in one or more intakes, in the absence of another active agent.

2. The method as claimed in claim 1, wherein the pharmaceutically acceptable iron salt is selected from ferrous salts and ferric salts.

3. The method of claim 2, wherein the pharmaceutically acceptable iron salt is selected from the group consisting of ferric ammonium citrate, ferric pyrophosphate, ferritin, ferrocholinate, ferrous ascorbate, ferrous aspartate, ferrous chloride, ferrous sulfate, ferrous tartrate, ferrous fumarate, ferrous gluconate, ferrous gluceptate, ferrous glycine sulfate, ferrous lactate, ferrous oxalate and ferrous succinate.

4. The method as claimed in claim 1, wherein the pharmaceutically acceptable iron atom is in the form of iron dextran, iron sucrose, iron polymaltose or iron sorbitol.

5. The method as claimed in claim 1, wherein the pharmaceutically acceptable organic iron is in the form of iron biglycinate, iron glycinate or iron protein succinylate.

6. The method as claimed in claim 1, wherein the iron is administered orally, anally, parenterally, intramuscularly or intravenously.

7. The method as claimed in claim 1, characterized in that iron is administered in a dosage that corresponds to a daily intake of ferrous sulfate of approximately 500 mg, in one or more intakes.

8. The method as claimed in claim 3, wherein the iron salt is ferrous sulfate.

9. The method of claim 8, wherein the ferrous sulfate is gastroprotected.

* * * * *